United States Patent [19]

Weston

[11] 4,294,842
[45] Oct. 13, 1981

[54] ANTI-PROTOZOAL OXADIAZOLE DERIVATIVES

[75] Inventor: John B. Weston, Tring, England

[73] Assignee: Burroughs Wellcome Co., Research Triangle Park, N.C.

[21] Appl. No.: 56,997

[22] Filed: Jul. 12, 1979

[30] Foreign Application Priority Data

Jul. 13, 1978 [GB] United Kingdom ............... 29818/78

[51] Int. Cl.³ ..................... A61K 31/42; C07D 271/06
[52] U.S. Cl. ...................................... 424/272; 548/131
[58] Field of Search ......................... 548/131; 424/272

[56] References Cited

U.S. PATENT DOCUMENTS 3,897,447  7/1975  Fisher et al. ......................... 548/131
4,067,988  11/1978 Buret et al. .......................... 548/131

FOREIGN PATENT DOCUMENTS 7529    2/1980   European Pat. Off. ............ 424/272
2347926 11/1977  France ................................ 548/131

OTHER PUBLICATIONS

Jaunin, "Chem. Abs.", vol. 64, (1966), p. 11197.
Haynes et al., "J. Med. Chem.", vol. 15, No. 11, (1972), pp. 1198–1200.
Derwent Copie of Belgium Pat. No. 840,719, and U.S. Pat. No. 3,907,807.

Primary Examiner—Anton H. Sutto

Attorney, Agent, or Firm—Donald Brown

[57] ABSTRACT

Anti-protozoal 1,2,4-oxadiazole derivatives of the formula

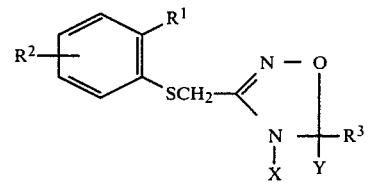

where $R^1$ is hydrogen, lower alkyl, halogen, hydroxy, alkoxy or nitro; each $R^2$ is the same or different in one or more of the 3,4,5 or 6 positions and is hydrogen, lower alkyl, halogen, hydroxy, aryloxy, alkylthio, arylthio, amino, substituted amino, cyano or nitro or two adjacent groups $R^2$ together form a residue —CH=CH—CH=CH—; or $R^1$ and one $R^2$ together form a residue —CH=CH—CH=CH—; $R^3$ is hydrogen, lower alkyl, aryl, substituted aryl or a group Ar SCH$_2$- were Ar is an unsubstituted or mono, di-or-tri-substituted phenyl group where the substituents are the same or different; and X and Y together form a bond or are each hydrogen; and acid addition salts thereof, methods for their preparation, formulations thereof and their use in the treatment of protozoal infections are described.

7 Claims, No Drawings

ANTI-PROTOZOAL OXADIAZOLE DERIVATIVES

The present invention relates to novel chemical compounds, methods for their preparation, formulations containing them and to their use in human and veterinary medicine.

More particularly the invention is concerned with 1,2,4-oxadiazole derivatives of formula (I) below which have been found to be active against protozoa; the compounds of the invention are thus potentially useful for the treatment of protozoal diseases in both man and other animals. Notable protozoal diseases include malaria in man and coccidiosis in poultry.

Compounds of formula (I) are:

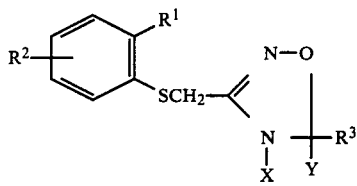

wherein
$R^1$ is hydrogen, lower alkyl, halogen, hydroxy, alkoxy or nitro;
each $R^2$ is the same or different in one or more of the 3,4,5, or 6-positions of the phenyl ring and is selected from hydrogen, lower alkyl, halogen, hydroxy, alkoxy, aryloxy, alkylthio, arylthio, amino, substituted amino, cyano or nitro on two adjacent groups $R^2$ together form a residue CH=CH—CH=CH;
or $R^1$ and one $R^2$ together form a residue —CH=CH—CH=CH;
X and Y together form a bond or X and Y are both hydrogen;
$R^3$ is hydrogen, lower alkyl, aryl, substituted aryl or a group —CH$_2$S-Ar; and
Ar is unsubstituted or mono-, di or tri-substituted phenyl wherein the substituents may be the same or different.

Acid addition salts of compounds of formula (I) which contain a basic group may also be prepared and such salts form a further aspect of the present invention.

Lower alkyl as used herein refers to an alkyl group having from 1 to 6 carbon atoms.

Substituted amino as used herein refers to a group —NH$_2$ where one or both of the hydrogen atoms is/are replaced by one or more residues containing carbon and hydrogen and which residues may themselves bear substituents.

Substituted amino thus includes for example, alkylamino (e.g. NHMe; —NMe$_2$), arylamino (e.g. —NHPh); aralkylamino (e.g. —NHCH$_2$Ph; —NHCH$_2$C$_6$H$_4$Cl), imino (e.g. —N=CHC$_6$H$_4$OMe; —N=CHC$_6$H$_3$(OMe)$_2$; —N=CH-C$_6$H$_4$Cl and substituted amino e.g. -NH(CH$_2$)$_n$NR$_2$, where n is an integer and R is lower alkyl).

The anti-protozoal activity of the compounds of formula (1) containing an amino group resides in the free base and thus the nature of the acid participating in any acid addition salts is of minor importance. In the preparation of the compounds of the invention acid addition salts of any kind may be prepared. However when such compounds of formula (I) are to be used in therapy the salts are preferably derived from nontoxic acids. The acids used will normally be those recognised to give pharmaceutically or veterinarily acceptable acid addition salts. Such acid addition salts include, for example, those derive from hydrochloric acid, hydroiodic acid, sulphuric acid, p-toluenesulphonic acid, maleic acid, lactic acid, citric acid, tartaric acid, succinic acid, oxalic acid and p-chlorobenzenesulphonic acid.

Particularly valuable compounds of formula (I) include:

3-Phenylthiomethyl-1,2,4-oxadiazole;
3-(4-Fluorophenylthiomethyl)-1,2,4-oxadiazole;
3-(2,3-Dimethylphenylthiomethyl)-1,2,4-oxadiazole;
3-(4-Bromophenylthiomethyl)-5-methyl-1,2,4-oxadiazole;
3,5-Di-(4-bromophenylthiomethyl)-1,2,4-oxadiazole; and
3,5-Di-(4-chlorophenylthiomethyl)-1,2,4-oxadiazole.

The compounds of formula (1) and, where obtainable, their acid addition salts may be prepared by any method known in the art for the preparation of compounds of analogous structure. In the following discussion of methods for the preparation of compounds of formula (I) it should be understood that where an intermediate has more than one reactive nitrogen atom it is desirable that the nitrogen atom not intended to participate in the reaction be protected by a suitable protecting group.

In particular compounds of formula (I) may be prepared by the reaction of an amidoxime of formula (II):

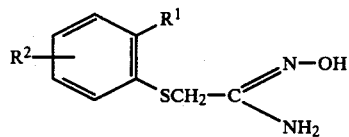

where $R^1$ and $R^2$ are as defined in formula (I) above either with an acylating agent of formula (III):

where $R^3$ is as defined in formula (I) above and Z is a leaving group, to give compounds where X and Y represent a bond; or an aldehyde or source thereof (e.g. formaldehyde paraformaldehyde), to give a compound where X and Y are both hydrogen.

The reaction may be carried out under conditions known in the art for conducting the Tiemann acylation synthesis. Thus suitable acylating agents include unsubstituted or substituted orthoesters, esters, carboxylic acids, carboxylic acid anhydrides and acid halides. The reaction may be effected in the absence or presence of an inert organic solvent (such as benzene or toluene) and is preferably effected at temperatures in the range of 60° to 200° C.

When the acylating agent is an orthoester the reaction is preferably carried out in the presence of an acid catalyst such as a mineral acid (e.g. sulphuric acid) or Lewis acid (e.g. boron trifluoride). When the acylating agent is an acyl halide the reaction is preferably conducted in the presence of an inorganic or organic base (e.g. trimethylamine).

It will of course be understood that in conducting this reaction the intermediate aryl compound of formula (IV) may be formed.

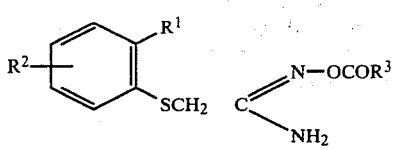

This compound may either be converted in situ to a compound of formula (1) or may be isolated and further reacted under suitable conditions to give a compound of formula (1).

Compounds of formula (I) where $R^3$ is hydrogen or lower alkyl may be prepared by the reaction of a compound of formula (V)

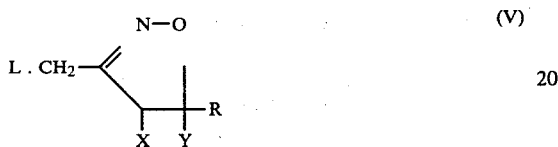

where X and Y are as defined in formula (I), L is a leaving group, e.g. halogen and R is hydrogen or lower alkyl with a thiophenol of formula (VI):

where $R^1$ and $R^2$ are as defined in formula (I) above. L is preferably chloro and the reaction is suitably carried out in the presence of an alkali metal (e.g. sodium) in an aliphatic alcohol (e.g. ethanol), preferably at ambient temperature.

Compounds of formula (I) where $R^2$ is substituted amino may be prepared from the corresponding unsubstituted amino compound of formula (VII):

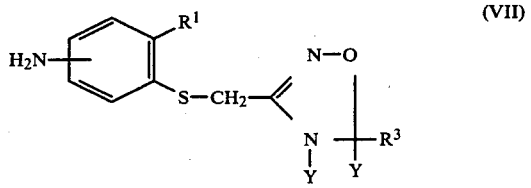

where $R^1$, $R^3$, X and Y are as defined in formula (I) above by methods known in the art for the conversion of the group —$NH_2$ to substituted amino groups. Suitable reagents for conversion of compounds of formula (VII) to such compounds of formula (I) include alkylating agents (to give alkylamines); aralkylating agents (to give aralkylamines) and aldehydes or aldehyde acetals (to give imino compounds). Such reactions may suitably be carried out in inert solvents (e.g. benzene, toluene) at elevated temperatures. The unsubstituted amino group may also be converted to a diazo group which may then be replaced by nucleophiles (e.g. $SCN^-$) to give further compounds of formula (I).

Compounds of formula (I) wherein $R^3$ is a group Ar—S—$CH_2$— may be prepared by the reaction of compound of formula (VIII)

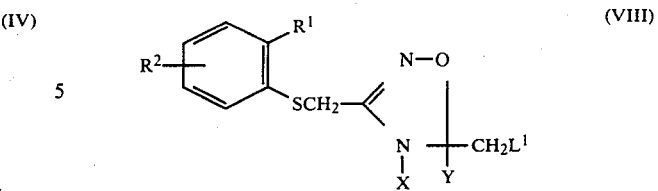

where $R^1$, $R^2$, X and Y are as defined in formula (I) above and $L^1$ is a leaving group, e.g. halogen (preferably chloro), with a thiophenol ArSH (where Ar is as defined in formula (I) above). The reaction conditions are suitably those used for the conversion of a compound of formula (V) to a compound of formula (I).

Compounds of formula (I) wherein $R^4$ is a methylthiophenyl group, which may be represented by the formula (IX)

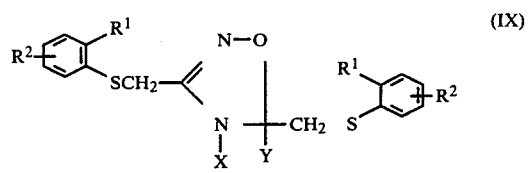

where $R^1$, $R^2$, X and Y are as defined in formula (I) above may be prepared by the reaction of a compound of formula (X)

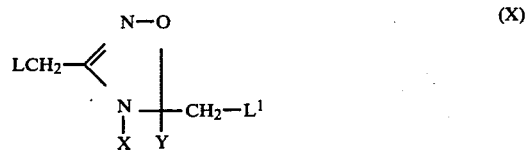

where X and Y are as defined in formula (I) above and L and $L^1$ are both leaving groups, e.g. halogen (preferably chloro), with two molar equivalents of a thiophenol of formula (IV) to give a compound of formula (1).

Compounds of formula (1) where X and Y are both hydrogen may be prepared by reaction of the oxadiazole analogue of formula (1) (where X and Y together represent a bond) with a reducing agent, notably sodium borohydride. The reaction may conveniently be carried out in an aliphatic alcohol, e.g. methanol, at elevated or, preferably, ambient temperature.

Where acid addition salts of the compounds of formula (1) may be obtained they may be prepared by any method known in the art for the preparation of such salts of analogous compounds. In particular they may be prepared by treatment of the free base with an appropriate acid or by metathesis.

While it is possible that, for use as antiprotozoal agents, the compounds of formula (1) and, where obtainable, their non-toxic acid addition salts (hereinafter referred to as "the active compounds") may be administered as the raw chemical it is preferable to present the active ingredient(s) as a pharmaceutical or veterinary formulation.

Pharmaceutical formulations comprise the active compound(s) together with one or more pharmaceutically acceptable carriers therefor and optionally other therapeutic and/or prophylactic ingredients. The carrier(s) must be "acceptable" in the sense of being compatible with the other ingredients of the formula and not deleterious to the recipient thereof.

It will be appreciated that the amount of active compound required for use in the treatment or prophylaxis of protozoal infections will vary not only with the nature of the active compound but also with the route of administration and the nature of the infection to be controlled. In general a suitable dose for a mammal (including man) for the treatment of protozoal infections (such as for example malaria) will lie in the range of 0.1 mg to 200 mg base/kilogram bodyweight, with a preferred range of 1 mg to 100 mg.

The active compound(s) may conveniently be presented (as a pharmaceutical formulation) in unit dosage form. A convenient unit dose formulation contains the active compound(s) in an amount of from 10 mg to 1 g.

The pharmaceutical formulation include those suitable for oral, rectal or parenteral (including intramuscular and intravenous) administration, although oral is the preferred route. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The veterinary formulations of the present invention are normally in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the active ingredient(s), and 0 to 50% w/w and preferably 20 to 40% w/w of conventional veterinary excipients. These powders may either be added to animal feeds stuffs for example by way of an intermediate premix or diluted in animal drinking water.

Liquid concentrates of this invention suitably contain a water soluble compound of formula (I) or veterinarily acceptable water soluble salt and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following Examples are given purely by way of illustration of the present invention and should not be construe in any way as constituting a limitation thereof. All temperatures are in degrees Celcius.

EXAMPLE I 3-(4-Methylphenylthiomethyl)-1,2,4-oxadiazole 2-(4-Methylphenylthiomethyl)acetamidoxime (5.9 g; 0.03 mol) was heated at 80° for 1 hour with triethyl orthoformate (8.8 g, 0.06 mol) and boron trifluoride etherate (0.1 ml). The solution thus obtained was evaporated to dryness to give a solid which on recrystallisation from propan-2-ol gave 3-(4-methylphenylthiomethyl)-1,2,4-oxadiazole, mp 53°.

EXAMPLE 2

3-(4-Methylphenylthiomethyl)-5-phenyl-1,2,4-oxadiazole (a) 2-(4-Methylphenylthiomethyl)acetamidoxime (4.9 g, 0.025 mol) and triethylamine (3.5 ml, 0.025 mol) were stirred in toluene at 0° C. A solution of benzoyl chloride (5.5 g, 0.025 mol) in toluene (10 ml) was added dropwise over ½ hour. A thick tan coloured precipitate formed and was removed by filtration, washed with water and recrustallised from isopropanol to give O-benzoyl-2-(4-methylphenylthio)acetamidoxime, m.p. 115.1° C.

(b) O-Benzoyl-2-(4-methylphenylthio)acetamidoxime (20 g, 0.06 mol) was refluxed gently in 1,4-dioxan (300 ml). After 2½ hours a dark red solution had formed. The solvent was removed to yield a dark-coloured oil which was chromatographed on silica gel (330 g) and eluted with ether/hexane (1:4). The solid product thus isolated was recrystallised from isopropanol to give 3-(4-methylphenylthiomethyl)-5-phenyl-1,2,4-oxadiazole, m.p. 71°.

EXAMPLE 3

3-(4-Bromophenylthiomethyl)-1,2,4-oxadiazole

Sodium (1.27 g) was dissolved in absolute ethanol (50 ml) and to this was added 4-bromothiophenol (11.18 g). When a solution had formed 3-chloromethyl-1,2,4-oxadiazole (6.5 g) was added dropwise with stirring over ten minutes, stirring was continued for a further 30 minutes, sodium chloride removed by filtration, the filtrate evaporated under reduced pressure and the residue recrystallised from isopropanol to give 3-(4-bromophenylthiomethyl)-1,2,4-oxadiazole, m.p. 56°.

By methods analogous to that described in Example 3 the following compounds were also prepared.

| Example No. | Compound |
| --- | --- |
| 4 | 3-Phenylthiomethyl-1,2,4-oxadiazole, m.p. 57°. |
| 5 | 3-(2-Bromophenylthiomethyl)-1,2,4-oxadiazole, m.p. 10°. |
| 6 | 3-(2-Methoxyphenylthiomethyl)-1,2,4-oxadiazole, m.p. 49°. |
| 7 | 3-(3-Phenylthiophenylthiomethyl)-1,2,4-oxadiazole, m.p. 53.5°. |
| 8 | 3-(3-Methylphenylthiomethyl)-1,2,4-oxadiazole, b.p. 128–132 (0.5mm Hg). |
| 9 | 3-(3-Aminophenylthiomethyl)-1,2,4-oxadiazole, m.p. 40°. |
| 10 | 3-(3-Methoxyphenylthiomethyl)-1,2,4-oxadiazole, m.p. 20°. |
| 11 | 3-(4-Methylphenylthiomethyl)-1,2,4-oxadiazole, m.p. 52°. |
| 12 | 3-(4-Nitrophenylthiomethyl)-1,2,4-oxadiazole, m.p. 113–115°. |
| 13 | 3-(4-Methoxyphenylthiomethyl)-1,2,4-oxadiazole, m.p. 42°. |
| 14 | 3-(4-Aminophenylthiomethyl)-1,2,4-oxadiazole, m.p. 46°. |
| 15 | 3-(4-Fluorophenylthiomethyl)-1,2,4-oxadiazole, m.p. 63°. |
| 16 | 3-(4-Methylthiophenylthiomethyl)-1,2,4-oxadiazole, m.p. 65°. |
| 17 | 3-(2,3-Dimethylphenylthiomethyl)-1,2,4-oxadiazole, m.p. 25°. |
| 18 | 3-(2,4-Dimethylphenylthiomethyl)-1,2,4-oxadiazole, b.p. 131–135°; (0.35 mm Hg). |
| 19 | 3-(1-Naphthylthiomethyl)-1,2,4-oxadiazole, m.p. 31°. |
| 20 | 3-(3,4-Dichlorophenylthiomethyl)-1,2,4-oxadiazole, m.p. 51°. |
| 21 | 3-(2,4-5-Trichlorophenylthiomethyl)-1,2,4-oxadiazole, m.p. 115°. |
| 22 | 3-(4-Bromophenylthiomethyl)-5-methyl-1,2,4-oxadiazole, m.p. 63°. |
| 23 | 3-(2,3-Dimethylphenylthiomethyl)-5-methyl-1,2,4-oxadiazole, m.p. 34°. |
| 24 | 3-(4-Nitrophenylthiomethyl)-5-methyl-1,2,4-oxadiazole, m.p. 90°. |
| 25 | 3-(4-Chlorophenylthiomethyl)-5-methyl-1,2,4-oxadiazole, m.p. 32°. |
| 26 | 3,5-Di-(4-bromophenylthiomethyl)-1,2,4-oxadiazole, m.p. 78°. |
| 27 | 3,5-Di-(4-chlorophenylthiomethyl)-1,2,4-oxadiazole, m.p. 56°. |
| 28 | 3-(4-Bromophenylthiomethyl)-5-phenyl-1,2,4-oxadiazole, m.p. 91°. |
| 29 | 3-(2-Hydroxyphenylthiomethyl)-1,2,4-oxadiazole, mass spectrum M + 1, 209; refractive index 1.6036. |
| 30 | 3-(2,6-Dimethylphenylthiomethyl)-1,2,4-oxadiazole, b.p. 111–117° (0.2mm Hg) |
| 31 | 3-(3-Trifluoromethylphenylthiomethyl)-1,2,4-oxadiazole, b.p. 117–118° (0.6mm Hg). |
| 32 | 3-(4-n-Butylphenylthiomethyl)-1,2,4-oxadiazole, b.p. 142° at 0.2mm Hg. |
| 33 | 3-(4-N,N-Dimethylaminophenylthiomethyl)-1,2,4-oxadiazole, m.p. 56.5–60° |
| 34 | 3-(4-t-Butylphenylthiomethyl)-1,2,4-oxadiazole, mass spectrum M + 1, 249; refractive index 1.5592. |
| 35 | 3-(4-Hydroxyphenylthiomethyl)-1,2,4-oxadiazole, m.p. 82° |
| 36 | 3-(4-Chlorophenylthiomethyl)-1,2,4-oxadiazole, m.p. 56°. |
| 37 | 3-(2-Bromo-5-methylphenylthiomethyl)-1,2,4-oxadiazole, m.p. 32°. |
| 38 | 3-(2-Naphthylthiomethyl)-1,2,4-oxadiazole, m.p. 76°. |

EXAMPLE 39

3-(4-Chlorophenylthiomethyl)-5-(2-dimethylaminophenylthiomethyl)-1,2,4-oxadiazole (a) 2-(4-Chlorophenylthio)acetamidoxime (21.7 g, 0.1 mol) was stirred in toluene (150 ml) whilst a solution of chloroacetyl chloride (11.3 g, 0.1 mol) in toluene (50 ml) was added dropwise over 20 minutes. The thick suspension was refluxed for 1 hour to give a black mixture which was cooled and then extracted with water and ether. The ether extracts were evaporated to give a brown oil which was chromatographed on silica gel (200 g) and eluted with ether/hexane (2:3) to give 5-chloromethyl-3-(4-chlorophenylthiomethyl)-1,2,4-oxadiazole.

(b) 2-Dimethylaminobenzenethiol (1.67 g, 0.011 mol) was dissolved in a solution of sodium methoxide (0.59 g) in methanol (50 ml) and 5-chloromethyl-3-(4-chlorophenylthiomethyl)-1,2,4-oxadiazole (3.0 g 0.011 mol) was added dropwise with stirring. After a further 10 min. stirring the solution was filtered and evaporated to leave a brown oil, which was purified by chromatography on silica gel elution with hexane/ether (3:2) giving 3-(4-chlorophenylthiomethyl)-5-(2-dimethylaminophenylthiomethyl)-1,2,4-oxadiazole as a colourless oil, mass spectrum M+1 392; refractive index 1.6263.

EXAMPLE 40

By the method described in Example 39, 5-(2-aminophenylthiomethyl)-3-(4-chlorophenylthiomethyl)-1,2,4-oxadiazole, mass spectrum M+1 364; refractive index 1.6488, was similarly prepared.

EXAMPLE 41

3,5-Di-(4-bromophenylthiomethyl)-1,2,4-oxadiazole

4-Bromobenzenethiol (3.78 g, 0.02 mol) was added to a solution of sodium (0.46 g, 0.02 mol) in ethanol (50 ml.) and 3,5-di-(chloromethyl)-1,2,4-oxadiazole (1.67 g, 0.01 mol) was added dropwise. The solution was then filtered and evaporated to give a solid which was recrystallised from isopropanol to give 3,5-di-(4-bromophenylthiomethyl)-1,2,4-oxadiazole, m.p. 80°.

EXAMPLE 42

By the method described in Example 41, 3,5-di-(4-chlorophenylthiomethyl)-1,2,4-oxadiazole m.p. 56° was similarly prepared.

EXAMPLE 43

4-5-Dihydro-3-(4-methylphenylthiomethyl)-1,2,4-oxadiazole 3-(4-Methylphenylthiomethyl)-1,2,4-oxadiazole (1.65 g, 0.008 mol) was dissolved in methanol (25 ml). AT 0° and with stirring, sodium borohydride (0.91 g, 0.024 mol) was added in portions over 30 min. The mixture was then stirred at 0° overnight and water then added to give a solid which on recrystallisation from from isopropanol gave 4.5-dihydro-3-(4-methylphenylthiomethyl)-1,2,4-oxadiazole, m.p. 85°.

EXAMPLE 44

By the method of Example 43 3-(4-aminophenylthiomethyl)-4,5-dihydro-1,2,4-oxadiazole, m.p. 106°, was similarly prepared.

EXAMPLE 45

3-(4-Thiocyanatophenylthiomethyl)-1,2,4-oxadiazole

Sodium nitrite (1.38 g, 0.02 mol) in water (15 ml) was added dropwise to a solution of 3-(4-aminophenylthiomethyl)-1,2,4-oxadiazole, (4.14 g, 0.02 mol) in acetic acid (120 ml) and 2 N sulphuric acid (40 ml) at 0° with stirring. The pale yellow solution thus obtained was added over 30 min. to a stirred mixture of cuprous thiocyanate (6 g) and potassium thiocyanate (60 g) in water (100 ml) at 0°, and the mixture stirred overnight. The mixture was then neutralised with solid sodium hydrogen carbonate and extracted with chloroform to give a yellow solid which was recrystallised from propan-2-ol to give 3-(4-thiocyanatophenylthiomethyl)-1,2,4-oxadiazole, m.p. 78°.

EXAMPLE 46

Groups of five mice were inoculated intraperitoneally with the normal strain of *P. berghei*. The mice on test received seven oral doses of drug begining on the afternoon of the day of infection then twice a day for the following three days. Blood parasitaemias were estimated on the fourth day and compared with those of the untreated controls.

The results are given in Table 1, the results being expressed as percentage inhibition of *P.berghei*.

EXAMPLE 47

Monolayer cultures of chick embryo liver cells were seeded onto microtitration plates and treated with the test compound (formulated by suspension in ethanol (0.05 ml) followed by dilution with sterile water (0.95 ml). Sporozoites of *Eimeria tenella* in culture medium were added and the culture fixed 90 hours after infection. The percentage inhibition compared to controls was determined, the results being expressed on a sacle of 0(0-10% inhibition) to 4(91-100% inhibition).

The results are given in Table 2.

TABLE 1

| Compound (Example No) | Percentage Inhibitions 7 × 100 mg/kg. |
|---|---|
| 1 | 38 |
| 3 | 71 |
| 4 | 49 |
| 5 | 2(7 × 80) |
| 6 | 5(7 × 50) |
| 7 | 2 |
| 9 | 34 |
| 12 | 14 |
| 14 | 41 |
| 15 | 59(7 × 50) |
| 16 | 4 |
| 17 | 62 |
| 18 | 14 |
| 19 | 55(7 × 50) |
| 21 | 19; 18(7 × 20) |
| 22 | 46 |
| 26 | 99 |
| 27 | 47 |
| 29 | 23 |

TABLE 1-continued

| Compound (Example No) | Percentage Inhibitions 7 × 100 mg/kg. |
|---|---|
| 33 | 19 |
| 34 | 28 |
| 38 | 21 |
| 40 | 18 |
| 44 | 10 |
| 45 | 34(7 × 10) |

TABLE 2

| Compound (Example No) | Index of Inhibition 20μg/ml |
|---|---|
| 5 | 1 |
| 7 | 1 |
| 8 | 3 |
| 9 | 2 |
| 10 | 4(5μg/ml) |
| 12 | 4 |
| 13 | 2 |
| 14 | 2 |
| 15 | 3 |
| 16 | 2 |
| 17 | 2 |
| 18 | 2 |
| 20 | 3 |
| 21 | 4 |
| 22 | 2 |

| Compound (Example 6 No) | Index of Inhibition 20μg/ml |
|---|---|
| 23 | 3 |
| 24 | 2 |
| 25 | 2 |
| 26 | 2 |
| 31 | 4 |
| 32 | 2 |
| 36 | 4(400ppm; in vivo) |
| 37 | 3;(2 at 5μg/ml) |
| 45 | 2 (5μg/ml). |

EXAMPLE 48

The $LD_{50}$ of the compound of Example 4 was determined in mice by conventional methods, the compound being administered orally as a suspension in 0.25% Celacol. An $LD_{50}$ of approx. 1600 mg/kg was determined.

EXAMPLE 49

| Tablet Formulation | |
|---|---|
| 3-Phenylthiomethyl-1,2,4-oxadiazole | 100 g |
| Lactose | 100 g |
| Starch | 30 g |
| Methylcellulose | 2 g |
| Magnesium Stearate | 2 g |

EXAMPLE 50

| Injectable Solution | |
|---|---|
| 3-(4-Aminophenylthiomethyl)-1,2,4-oxadiazole hydrochloride | 10 g |
| Chlorocresol. | 0.1 g |
| Water for Injections to produce | 100 ml. |

EXAMPLE 51

| Dispersible Granules | Parts by weight |
|---|---|
| 3-(4-Aminophenylthiomethyl)-1,2,4-oxadiazole | 50 |
| Lactose | 49 |
| Povidone | 1 |

We claim:

1. A compound of the formula (I)

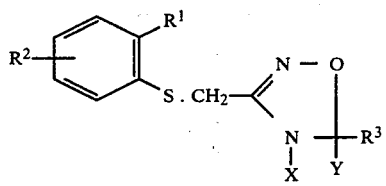

wherein $R^1$ is selected from the group consisting of hydrogen, lower alkyl, halogen, hydroxy, alkoxy or nitro;

each $R^2$ is the same or different and is selected from the group consisting of hydrogen, lower alkyl, halogen, hydroxy, alkoxy, aryloxy, alkylthio, arylthio, amino, substituted amino, cyano, nitro or together with an adjacent group $R^2$ a residue —CH=CH—CH=CH—;

or $R^1$ and one $R^2$ together form a residue —CH=CH—CH=CH—;

X and Y together represent a bond or are both hydrogen;

$R^3$ is selected from the group consisting of hydrogen, lower alkyl, aryl, and a group Ar—S.CH$_2$—; and Ar is phenyl optionally substituted with one, two or three substituents which may be the same or different, and acid addition salts thereof.

2. A compound of formula (I) according to claim 1 wherein X and Y are both hydrogen.

3. A compound of formula (I) according to claim 1 or claim 2 wherein $R^3$ is hydrogen.

4. A compound of formula (I) according to claim 1 and selected from the group consisting of 3-phenylthiomethyl-1,2,4-oxadiazole, 3-(4-fluorophenylthiomethyl)-1,2,4-oxadiazole, 3-(2,3-dimethylphenylthiomethyl)-1,2,4-oxadiazole, 3-(4-bromophenylthiomethyl)-5-methyl -1,2,4-oxadiazole, 3,5-di(4-bromophenylthiomethyl)-1,2,4-oxadiazole and 3,5-di-(4-chlorophenylthiomethyl)-1,2,4-oxadiazole.

5. A pharmaceutical formulation for the treatment of protozoal infections in mammals comprising from 10 mg to 1 g of a compound as defined in any one of claims 1 to 4 or a pharmaceutically acceptable acid addition salt thereof together with a pharmaceutically acceptable carrier therefor.

6. A veterinary formulation for the treatment of protozoal infections in mammals or birds comprising from 50 to 100% w/w of a compound as defined in any one of claims 1 to 4 and from 0 to 50% w/w of a veterinarily acceptable carrier therefor.

7. A method for the treatment of a protozoal infection in animal, including man, comprising administration of a non-toxic antiprotozoal-effective amount of a compound as defined in any one of claims 1 to 4.

* * * * *